United States Patent [19]

Folkers et al.

[11] 3,953,416

[45] Apr. 27, 1976

[54] SYNTHETIC DECAPEPTIDE HAVING THE ACTIVITY OF THE LUTEINIZING HORMONE RELEASING HORMONE AND METHOD FOR MANUFACTURING THE SAME

[76] Inventors: Karl Folkers, 6406 Mesa Drive, Austin, Tex.; Bruce L. Currie, 8304 Kromer, Austin, Tex. 78758; Jaw-Kang Chang, 151 Calderon Ave., Mountain View, Calif. 94041; Hans Sievertsson, Lomvagen 77, 191 56 Sollentuna; Conny Bogentoft, Satunavagen 19 A, 19500 Marsta, both of Sweden

[22] Filed: Jan. 14, 1974

[21] Appl. No.: 432,903

Related U.S. Application Data

[63] Continuation-in-part of Ser. No. 210,122, Dec. 20, 1971, abandoned, which is a continuation of Ser. No. 158,996, July 1, 1971, abandoned.

[52] U.S. Cl. ................... 260/112.5 LH; 424/177
[51] Int. Cl.² ................. C07C 103/52; C07G 7/00
[58] Field of Search .......................... 260/112.5

[56] References Cited
UNITED STATES PATENTS

| | | | |
|---|---|---|---|
| 3,778,427 | 12/1973 | Flouret | 260/112.5 |
| 3,780,014 | 12/1973 | Flouret | 260/112.5 |
| 3,781,272 | 12/1973 | Flouret | 260/112.5 |
| 3,787,385 | 1/1974 | Folkers et al. | 260/112.5 |
| 3,787,386 | 1/1974 | Flouret et al. | 260/112.5 |
| 3,790,554 | 2/1974 | Flouret | 260/112.5 |
| 3,790,555 | 2/1974 | Flouret | 260/112.5 |
| 3,796,697 | 3/1974 | Flouret | 260/112.5 |
| 3,803,117 | 4/1974 | Flouret | 260/112.5 |
| 3,826,794 | 7/1974 | Flouret | 260/112.5 |
| 3,826,796 | 7/1974 | Sarantakis et al. | 260/112.5 |
| 3,855,198 | 12/1974 | Sarantakis | 260/112.5 |
| 3,856,769 | 12/1974 | Sakakibara et al. | 260/112.5 |

OTHER PUBLICATIONS
Chem. Eng. News, 49, 7 (1971).
Matsuo et al., Biochem. Biophys. Res. Comm., 43, 1334–1339 (1971).

*Primary Examiner*—Lewis Gotts
*Assistant Examiner*—Reginald J. Suyat
*Attorney, Agent, or Firm*—Salvatore C. Mitri

[57] ABSTRACT

A synthetic decapeptide, L-pglutamyl-L-histidyl-L-tryptophanyl-L-seryl-L-tyrosyl-glycyl-L-leucyl-L-arginyl-L-prolyl-glycinamide which has the hormonal activities of the luteinizing hormone releasing hormone (LRH) of the hypothalamus gland of mammals is produced by utilizing as the key starting materials, the amino acids, glutamic acid or pyroglutamic acid, histidine, tryptophan, serine, tyrosine, glycine, leucine, arginine, and proline. Synthesis of the decapeptide is accomplished by coupling, in appropriate combinations of appropriate protected forms of the amino acids, and finally deprotecting to yield the amide, tyrosyl-glycyl-L-leucyl-L-arginyl-L-prolyl-glycinamide.

4 Claims, No Drawings

SYNTHETIC DECAPEPTIDE HAVING THE ACTIVITY OF THE LUTEINIZING HORMONE RELEASING HORMONE AND METHOD FOR MANUFACTURING THE SAME

This application is a continuation-in-part of co-pending application Ser. No. 210,122 filed Dec. 20, 1971, now abandoned which application in turn is a continuation of prior application Ser. No. 158,996 filed July 1, 1971, now abandoned.

This invention relates to the decapeptide, L-pglutamyl-L-histidyl-L-tryptophanyl-L-seryl-L-tyrosyl-glycyl-L-leucyl-L-arginyl-L-prolyl-glycinamide, which is referred to hereinafter as the "decapeptide-$NH_2$," and to alternative methods for its synthesis. This synthetic decapeptide, decapeptide-$NH_2$, has the same biological and hormonal activities as does the naturally occurring luteinizing hormone releasing hormone of the hypothalamus in the brain of mammals including man. This hormone is referred to herinafter as "LRH".

BACKGROUND OF THE INVENTION

The luteinizing hormone releasing hormone (LRH) is well recognized to be one of the neurohormones of the hypothalamus of mammalian species, including man. The hypothalamus is a part of the forebrain, prosencephalon, which unlike the cerebellum and the cerebral hemispheres, has maintained throughout its phylogenetic history a relative constancy of arrangement. Basically, the hypothalamus is divisible into medial and lateral portions. The medial division joins the third ventricle. The lateral portion of the hypothalamus contains cells that are diffusely arranged among the fibers of what has long been called the medial forebrain bundle. An anatomic relationship which is a constant feature of the hypothalamus is its intimate association with the pituitary gland. The pituitary gland consists of the posterior and anterior lobes. Biochemical transport of the neurohormones of the hypothalamus to the anterior lobe is provided by certain blood vessels in a portal system which is a network of capillaries. The blood of these capillaries passes down the pituitary stalk and becomes distributed through another system of capillaries in the anterior lobe and one of the neurohormones thus transported in LRH.

In addition to LRH, there is believed to be a prolactin releasing hormone (PRH). It is generally considered that there is one hypothalamic releasing hormone for each of the pituitary hormones of the anterior lobe, but this concept has not yet been proven and, indeed, LRH may release both LH and FSH. However, it has been established that there is a hypothalamic neurohormone which releases the luteinizing hormone of the anterior pituitary; that is, LRH. It appears that LRH also releases FSH, at least to some extent.

Presently, LRH is extracted from animal hypothalamic tissue obtained from many thousands of animals at slaughter houses with great difficulty since the size of the hypothalamic tissue from a full grown pig is only about 150 mg. The enormous task involved in obtaining pure LRH from animal tissue is exemplified by the fact that less than 0.5 mg. of purified, but not completely pure, LRH was obtained from the combined tissue of about 80,000 sheep. (Guillemin, *International Journal of Fertility*, Vol. 12, No. 4, pp. 359 (1967).) Guillemin stated that "the difficulties involved in the isolation of LRH are such, however, that we must consider as absolutely out of the question the use of hypothalamic hormones of natural sources for our clinical studies." It can be seen, therefore, that scientifically, LRH has been obtained in only very minute amounts and incompletely freed of impurities. Thousands, and sometimes hundreds of thousands, of hypothalamic fragments from as many animals are required to obtain minute quantities of the natural hormone and even then it is of still doubtful chemical purity.

Working initially with 165,000 pig hypothalami, Schally, et al. (Biochem. *Biophys. Res. Commun.*, 43, (2), 393 (1971)), ultimately obtained 830 $\mu$g of material which still was not completely pure, but which released both LH and FSH. This very limited quantity of material represented purification of over 2 million-fold.

It is clearly evident that the naturally occurring LRH derived from slaughter house tissue can hardly be obtained in sufficient quantity and purity to permit even the most exploratory diagnostic studies in medicine, and that obtaining LRH from this tissue for widespread practical use in medicine is impossible.

THE INVENTION

It has been found now that the decapeptide, L-pglutamyl-L-histidyl-L-tryptophanyl-L-seryl-L-tyrosyl-glycyl-L-leucyl-L-arginyl-L-prolyl-glycinamide, can be synthetically produced by utilizing starting materials which are both readily available or readily producible. The basic starting materials that can be utilized to synthesize the decapeptide of this invention are the following ten amino acids:
   glutamic acid (Glu—)
or
   p-glutamic acid (pGlu—)
   histidine (His—)
   tryptophan (Trp—)
   serine (Ser—)
   tyrosine (Tyr—)
   glycine (Gly—)
   leucine (Leu—)
   arginine (Arg—)
   proline (Pro—)

These nine amino acids can be used in appropriately protected forms for synthesis of units of peptides which are then combined and then deprotected to give the decapeptide-$NH_2$. For example:

The two pentapeptides, one beginning with pyroglutamic acid and the other ending with glycine, in their appropriately protected forms, can be coupled and deprotected to yield the decapeptide-$NH_2$.

Alternatively, the hexapeptide ending with glycine and the tetrapeptide beginning with pyroglutamic acid, in appropriately protected forms may be coupled, and deprotected, to yield the decapeptide-$NH_2$.

Alternatively, the heptapeptide ending with glycine and the tripeptide beginning with pyroglutamic acid, in their appropriately protected forms, may be coupled, and deprotected, to yield the decapeptide-$NH_2$.

Alternatively, the octapeptide ending with glycine and the dipeptide beginning with pyroglutamic acid, in their appropriately protected forms, may be coupled, and deprotected, to give the decapeptide-$NH_2$.

Alternatively, the nonapeptide ending with glycine and the amino acid, pyroglutamic acid, in their appropriately protected forms, may be coupled, and deprotected, to give the decapeptide-$NH_2$.

Alternatively, the hexapeptide beginning with pyroglutamic acid and the tetrapeptide ending with glycine, in their appropriately protected forms, may be coupled, and deprotected, to give the decapeptide-$NH_2$; also, the hexapeptide beginning with pyroglutamic acid and the tetrapeptide ending with glycine, in their unprotected forms, may be coupled to give the decapeptide $NH_2$.

Alternatively, the heptapeptide beginning with pyroglutamic acid and the tripeptide ending with glycine, in their appropriately protected forms, may be coupled, and deprotected, to give the decapeptide-$NH_2$.

Alternatively, the octapeptide beginning with pyroglutamic acid and dipeptide ending with glycine, in their appropriately protected forms may be coupled, and deprotected, to the decapeptide-$NH_2$.

Alternatively, the nonapeptide beginning with pyroglutamic acid and glycine, in their appropriately protected forms, may be coupled, and deprotected, to give the decapeptide-$NH_2$.

Alternatively, the heptapeptide in appropriately protected forms resulting from the solid-phase synthesis utilizing a resin carrier, and ending with glycine may be coupled with a tripeptide beginning with pyroglutamic acid, and the product may be deprotected to the decapeptide-$NH_2$.

These alternative steps of manufacturing the decapeptide-$NH_2$ consist of combining two peptides of five amino acids each as described in Example 1; combining the last six amino acids ending in Gly and in peptide formation with the first four amino acids beginning with pGlu and in peptide formation as described in Example 2; combining the last seven amino acids ending with Gly and the first three amino acids beginning with pGlu as described in Example 3; the last eight amino acids ending with Gly and the first two amino acids beginning with pGlu as described in Example 4; coupling the last nine amino acids ending in Gly with the first amino acid, pGlu, as described in Example 5; coupling the first six amino acids beginning with pGlu with the last four amino acids ending with Gly as described in Example 6; combining the first seven amino acids beginning with pGlu with the last three amino acids ending with Gly as in Example 7; coupling of the first eight amino acids beginning with pGlu with the last two amino acids ending with Gly as in Example 8; coupling the last amino acids, Gly, with the first nine amino acids ending with Pro, as described in Example 9; and by coupling the last seven amino acids ending with Gly from solid phase synthesis with the first three amino acids beginning with pGlu as described in Example 10.

The decapeptide-$NH_2$ of this invention is readily obtained, upon manufacturing scale, in pure form by the organic syntheses as described in greater detail herein below. The synthetic decapeptide-$NH_2$ readily lends itself to practicality in veterinary, agricultural, and medical fields and uses. The decapeptide-$NH_2$ is very useful to promote ovulation in mammalian species and in humans. It can overcome some causes of infertility and erratic fertility in women. In agricultural animals, it is useful to synchronize the fertility of animals in herds for breeding purposes and practicalities, and to induce fertility in rare and/or expensive animals such as valuable breeding stock. It can be used to increase the number of newborn animals in a litter from sows which is a matter of economic importance and particularly to increase twining in cows which is a matter of great economic importance; it can also be used to increase the number of newborn animals from ewes. The synthetic, decapeptide-$NH_2$, performs the hormonal functions of the natural LRH and can now be made commercially available on an economical cost basis and it offers a great advantage over the natural LRH which, as indicated above, has been available only with great difficulty on a scientific basis and not at all on a practical basis for use in veterinry medicine, agriculture, and/or humans.

The first nine examples given below are provided to exemplify the invention, and modifications of these examples in terms of the sequential uses of the amino acids, their protection and deprotection, as well as the selection of experimental conditions as to reaction time, temperature, solvents, and other experimental details are all considered in the scope of the invention. While all of these alternatives are successful, in principle, some of the alternatives are more practical for manufacturing purposes than other.

Example 10 is given below to exemplify utilizing the solid-phase synthesis to manufacture a part of the sequence of the decapeptide-$NH_2$ and then removing the partial sequence from the resin and then coupling with the remaining amino acids singly or in combination to complete the sequence of the decapeptide-$NH_2$ and with intermediate protection and appropriate deprotection. Specifically, Example 10 describes the obtaining of the heptapeptide ending with Gly from solid-phase synthesis and combining it with the tripeptide beginning with pGlu and then deprotecting the product to obtain the decapeptide-$NH_2$ directly or by intermediate steps of ester formation and amide formation to yield the final decapeptide-$NH_2$.

The following 10 examples are presented to illustrate methods of carrying out the present invention, and it should be understood that the protective groups described in the examples are only illustrative and are not intended to be limitative of the protective groups that can be used to carry out the present invention. Additional applicable protective groups which fall within the scope of this invention include, but are not limited to such groups as carbobenzyloxy-, tosyl-, phthalyl-, benzyl- and para-substituted benzyl groups ($CH_3O$—, Br—, etc.), trityl-, formyl-, t-butyloxycarbonyl- for protection of -$NH_2$ groups; as salt formation, Me ester, Et ester, benzyl ester, t-butyl ester, and hydrazide for protection of —COOH groups; as O-Acyl- (Acetyl, benzoyl-), O-Alkyl- (H- or benzyl-), for protection of the hydroxyl group of tyrosine and serine; as nitro-, carbobenzyloxy-, adamantyloxycarbonyl-, and protonation for protection of the guanidine moiety of arginine; as benzyl-, tosyl-, and dinitrophenyl for protection of the imidazole moiety of histidine.

EXPERIMENTAL PROCEDURES

The Synthesis of
L-Pyroglutamyl-L-Histidyl-L-Tryptophyl-L-Seryl-L-Tyrosylglycyl-L-Leucyl-L-Arginyl-L-Prolylglycinamide Chart I; Example I.

L-Pyroglutamyl-L-histidyl-L-tryptophan benzyl ester
(III)

L-Tryptophan benzyl ester (II) hydrochloride (0.33 g) and L-pyro-glutamyl-L-histidine (Chang, J.K., Sievertsson, H., Currie, B., and Folkers, K., J. Med. Chem., 14, 484 (1971)) (I) (0.266 g) in dry acetonitrile (50 ml) is treated with triethylamine (0.14 ml) and dicyclohexylcarbodiimide (DCI) (0.227 g) in dry acetonitrile (5 ml) at 0°C. After being stirred at room temperature for 24 hours, the reaction mixture is evaporated to dryness. The residue is dissolved in methanol and the dicyclohexylurea is removed by filtration. The mother liquor is concentrated and L-pyroglutamyl-L-histidyl-L-tryptophan benzyl ester (III) precipitated by addition of ethyl ether. The residue was partitioned with $CHCl_3$ and $H_2O$, and an oily product was separated between these 2 solvents. The oily product was collected and purified by recrystallization from MeOH-EtOAc to afford the tripeptide (yield 79%), mp 235°–238° dec, $[\alpha]^{22}D$ -6.8° (c 1.54, glacial HOAc), $R_f^1$ 0.72, $R_f^2$ 0.89, and $R_f^3$ 0.59, single spot with Pauly, Ehrlich, Cl-tolidine, and $I_2$ reagents.

Anal. Calcd. for $C_{29}H_{30}N_6O_5 \cdot H_2O$: C, 62.13; H, 5.73; N, 14.99. Found: C, 62.36; H, 5.86; N, 14.72.

L-Pyroglutamyl-L-histidyl-L-tryptophan (IV)

L-Pyroglutamyl-L-histidyl-L-tryptophan benzyl ester (III) (0.542 g) in absolute methanol (20 ml) is hydrogenated at room temperature and one atmosphere pressure in the presence of 5 percent palladium on charcoal (0.542 g) for 2 hours. The reaction mixture is filtered and evaporated to the tripeptide IV. (yield 64%), mp 188°–190° dec, $R_f^1$ 0.58, $R_f^2$ 0.64, $R_f^3$ 0.50, single spot with Pauly, Ehrlich, and Cl-tolidine reagents.

Anal. Calcd. for $C_{22}H_{24}N_6O_5 \cdot MeOH$: C, 58.83; H, 6.06; N, 16.85. Found: N, 16.84.

L-Pyroglutamyl-L-histidyl-L-tryptophyl-L-serine methyl ester (VI)

L-Pyroglutamyl-L-histidyl-L-tryptophan (IV) (0.452 g) and L-serine methyl ester (V) hydrochloride (0.155 g) in dry acetonitrile (50 ml) are treated with triethylamine (0.14 ml) and DCI (0.227 g) in dry acetonitrile (5 ml) at 0°C. After stirring at room temperature for 24 hours, the reaction mixture is evaporated to dryness. The residue is dissolved in methanol and the dicyclohexylurea is removed by filtration. The filtrate is concentrated to dryness to L-pyroglutamyl-L-histidyl-L-tryptophyl-L-serine methyl ester (VI).

L-Pyroglutamyl-L-histidyl-L-tryptophyl-L-serine (VII)

A solution of L-pyroglutamyl-L-histidyl-L-tryptophyl-L-serine methyl ester (VI) (0.553 g) in absolute methanol (50 ml) containing sodium hydroxide (40 mg) is stirred at room temperature for 2 hours. The reaction mixture is then neutralized to pH 7.5 with dilute hydrochloric acid and evaporated to dryness. The solid residue is triturated thoroughly in absolute methanol and filtered. The filtrate is evaporated to the tetrapeptide VII.

L-Pyroglutamyl-L-histidyl-L-tryptophyl-L-seryl-O-benzyl-L-tyrosine benzyl ester (IX)

O-Benzyl-L-tyrosine benzyl ester (VIII) hydrochloride (0.397 g) and L-pyroglutamyl-L-histidyl-L-tryptophyl-L-serine (VII) (0.539 g) in dry dimethylformamide (50 ml) is treated with triethylamine (0.14 ml) and dicyclohexylcarbodiimide (0.227 g) in dry dimethylformamdie (5 ml) at 0° C. After stirring at room temperature for 24 hours, the reaction mixture is evaporated to dryness. The residue is triturated in methanol and the dicyclohexylurea is removed by filtration. The filtrate is concentrated to L-pyroglutamyl-L-histidyl-L-tryptophyl-L-seryl-O-benzyl-L-tyrosine benzyl ester (IX).

L-Pyroglutamyl-L-histidyl-L-tryptophyl-L-seryl-L-tyrosine (X)

L-Pyroglutamyl-L-histidyl-L-tryptophyl-L-seryl-O-benzyl-L-tyrosine benzyl ester (IX) (0.882 g) in absolute methanol (100 ml) is hydrogenated at room temperature and one atmosphere pressure in the presence of 5 percent palladium on charcoal (0.882 g) for 2 hours. The reaction mixture is filtered and evaporated to the pentapeptide X.

$N^\alpha$-Carbobenzoxy-$N^\delta$,$N^\omega$-bis[adamantyl-(1)-oxycarbonyl]-L-arginyl-L-prolylglycinamide (XIII)

$N^\alpha$-Carbobenzoxy-$N^\delta$, $N^\omega$-bisadamantyloxycarbonyl-L-arginyl-N-hydroxysuccinimide ester (Jäger, G. and Geiger, R., Chem. Ber., 103, 1729 (1970)) (XI) (0.78 g) and L-prolylglycinamide (Jaquenand, P. A. and Boissonnas, R. A., Helv. Chim. Acta, 45, 1462 (1962)) (XII) (0.17 g) are mixed in 90 ml of dimethylformamide (DMF) at 0°. The mixture is stirred at room temperature overnight and then evaporated in vacuo. The residue is washed with water and the product is crystallized from ethanol and water to give the tripeptide XIII.

$N^\delta$, $N^\omega$-bis[adamantyl-(1)-oxycarbonyl]-L-arginyl-L-prolylglycinamide (XV)

$N^\alpha$-Carbobenzoxy-$N^\delta$, $N^\omega$-bisadamantyloxycarbonyl-L-arginyl-L-prolyl-glycinamide (XIII) (0.82 g) is dissolved in 50 ml of methanol and palladium on charcoal (5%) is added. The solution is hydrogenated at one atmosphere pressure and at room temperature for 1 hour. Evaporation of the solvent gives XV.

N-Carbobenzoxy-L-leucyl-$N^\delta$, $N^\omega$-bis[adamantyl-(1)-oxycarbonyl]-L-arginyl-L-prolylglycinamide (XVI)

N-Carbobenzoxy-L-leucine paranitrophenyl ester (Bodanszky, M. and du Vigneaud, V., Biochem. Prep., 9, 110 (1962)) (0.373 g) and $N^\delta$, $N^\omega$-bisadamantyloxycarbonyl-L-arginyl-L-prolylglycinamide (XV) (0.70 g) are mixed in 10 ml of DMF at 0°. The mixture is stirred at room temperature overnight and then evaporated in vacuo. The residue is treated with water and the product crystallized from ethanol and water.

L-Leucyl-$N^\delta$, $N^\omega$-bis[adamantyl-(1)-oxycarbonyl]-L-arginyl-L-prolyl-glycinamide (XVIII)

Carbobenzoxy-L-leucyl-$N^\delta$, $N^\omega$-bisadamantyloxycarbonyl-L-arginyl-L-prolylglycinamide (XVI) (0.93 g) in 50 ml of methanol is hydrogenated at one atmosphere pressure and at room temperature in the presence of 5% palladium on charcoal for one hour. The catalyst is removed by filtration. Evaporation of the solvent gives XVIII.

N-Carbobenzoxyglycyl-L-leucyl-$N^\delta$, $N^\omega$-bis[adamantyl-(1)-oxycarbonyl]-L-arginyl-L-prolylglycinamide (XIX)

N-Carbobenzoxyglycine paranitrobenzyl ester (XVII) Bodanszky, M. and du Vigneaud, V., Biochem. Prep. 9, 110 (1967)) (0.36 g) and L-leucyl-$N^\delta$, $N^\omega$-bisadamantyloxycarbonyl-L-arginyl-L-prolylglycinamide (XVIII) (0.81 g) are mixed in 10 ml of DMF at 0° C. The solution is stirred overnight and is evaporated in vacuo. The residue is treated with water and the product is crystallized from methanol and water.

Glycyl-L-leucyl-N$^\delta$,N$^\omega$-bis[adamantyl-(1)-oxycarbonyl]-L-arginyl-L-prolylglycinamide (XX)

N-Carbobenzoxyglycyl-L-leucyl-N$^\delta$,N$^\omega$-bisadamantyloxycarbonyl-L-arginyl-L-prolylglycinamide (XIX) (1.01 g) in 50 ml of methanol is hydrogenated in the presence of 5% palladium on charcoal for 1 hour at one atmosphere pressure and at room temperature. Filtration and evaporation of the solvent gives the pentapeptide XX.

L-Pyroglutamyl-L-histidyl-L-tryptophyl-L-seryl-L-tyrosylglycyl-L-leucyl-N$^\delta$,N$^\omega$-bis[adamantyl-(1)-oxycarbonyl]-L-arginyl-L-prolylglycinamide (XXI)

A solution of L-pyroglutamyl-L-histidyl-L-tryptophyl-L-seryl-L-tyrosine (X) (0.702 g) and glycyl-L-leucyl-N$^\delta$,N$^\omega$-bisadamantyloxy-carbonyl-L-arginyl-L-prolylglycinamide (XX) (0.853 g) in dry DMF (45 ml) is treated with DCI (0.227 g) in dry DMF (5 ml). After being stirred at room temperature for 24 hours, the reaction mixture is evaporated to dryness. The residue is dissolved in methanol and the dicyclohexylurea is removed by filtration. The mother liquor is evaporated to the blocked decapeptide XXI.

L-Pyroglutamyl-L-histidyl-L-tryptophyl-L-seryl-L-tyrosylglycyl-L-leucyl-L-arginyl-L-prolylglycinamide (XXII)

A solution of L-pyroglutamyl-L-histidyl-L-tryptophyl-L-seryl-L-tyrosylglycyl-L-leucyl-N$^\delta$,N$^\omega$-bisadamantyloxycarbonyl-L-arginyl-L-prolylglycinamide (XXI) (1.54 g) in trifluoroacetic acid (TFA) (5 ml) is allowed to stand at room temperature for 15 minutes. Absolute ethyl ether (25 ml) is then added to the reaction mixture and the precipitate is collected by filtration and washed thoroughly with absolute ethyl ether. The precipitate is dried in vacuo to give L-pyroglutamyl-L-histidyl-L-tryptophyl-L-seryl-L-tyrosylglycyl-L-leucyl-L-arginyl-L-prolylglycinamide XXII.

CHART II; EXAMPLE II.

N-Carbobenzoxy-O-benzyltyrosine (XXIII) is coupled with glycyl-leucyl-N$^\delta$,N$^\omega$ bis[adamantyl-(1)-oxycarbonyl]-arginyl prolylglycinamide XX via the DCI method to give the protected hexapeptide XXIV, which is then subjected to hydrogenolysis with 5% palladium on charcoal for removal of the carbobenzoxy and O-benzyl group. The resulting hexapeptide tyrosylglycylleucyl-N$^\delta$,N$^\omega$-bis[adamantyl-(1)-oxycarbonyl]-arginylprolylglycinamide XXV is coupled with pyroglutamylhistidyltryptophylserine (XII) affording pyroglutamylhistidyltryptophylseryltyrosylglycylleucyl-N$^\delta$,N$^\omega$-bis[adamantyl-(1)-oxycarbonyl]-arginyl-prolylglycinamide (XXI). This protected decapeptide XXI is converted successively into pyroglutamylhistidyltryptophylseryltyrosylglycylleucylarginylprolylglycinamide XXII as shown in Chart I; Example I.

CHART III; EXAMPLE III.

N-Carbobenzoxyseryltyrosine (XXVI) is coupled with glycylleucyl-N$^\delta$,N$^\omega$-bis[adamantyl-(1)-oxycarbonyl]-arginylprolylglycinamide (XX) via the DCI method to give the protected heptapeptide XXVII, which is then subjected to hydrogenolysis with 5% palladium on charcoal for removal of the carbobenzoxy group. The resulting peptide seryltyrosylglycylleucyl-N$^\delta$,N$^\omega$-bis[adamantyl-(1)-oxycarbonyl]-arginyl-prolylglycinamide XXVIII is coupled with pyroglutamylhistidyltryptophan to afford pyroglutamylhistidyltryptophylseryltyrosylglycylleucyl-N$^\delta$, N$^\omega$-bis[adamantyl-(1)-oxycarbonyl]-arginylprolylglycinamide (XXI). This protected decapeptide XXI is converted into pyroglutamylhistidyltryptophylseryltyrosylglycylleucylarginylprolylglycinamide (XXII) as shown in Chart I; Example I.

Chart IV; EXAMPLE IV.

N-Carbobenzoxytryptophan (XXIX) is coupled via the DCI method with seryltyrosylglycylleucyl-N$^\delta$,N$^\omega$-bis[adamantyl-(1)-oxycarbonyl]-arginylprolyl-glycinamide XXVIII affording the protected octapeptide XXX, which is subjected to hydrogenolysis with 5% palladium on charcoal for removal of the carbobenzoxy group. The obtained octapeptide, tryptophylseryltyrosylglycylleucyl-N$^\delta$, N$^\omega$-bis[adamantyl-(1)-oxycarbonyl]-arginylprolylglycinamide (XXXI) is coupled with pyroglutamylhistidine (I) via the DCI method to give pyroglutamylhistidyltryptophylseryltyrosylglycylleucyl-N$^\delta$, N$^\omega$-bis[adamantyl-(1)-oxycarbonyl]-arginylprolylglycinamide (XXI). The protected decapeptide XXI is converted to pyroglutamylhistidyltryptophylseryltyrosylglycylleucylarginylprolylglycinamide (XXII) as is shown in Chart I; Example I.

CHART V; EXAMPLE V.

N-Carbobenzoxyhistidine (XXXII) is coupled with tryptophylseryltyrosylglycylleucyl-N$^\delta$, N$^\omega$-bis[adamantyl-(1)-oxycarbonyl]-arginylprolylglycinamide (XXXI) via the DCI method to give the protected nonapeptide XXXIII, which is hydrogenated with 5% palladium on charcoal for the removal of the carbobenzoxy group. The obtained nonapeptide, histidyltryptophylseryltyrosylglycylleucyl-N$^\delta$, N$^\omega$-bis[adamantyl-(1)-oxycarbonyl]-arginyl prolylglycinamide XXXV is reacted with the activated ester of pyroglutamic acid from pentachlorophenol to afford pyroglutamylhistidyltryptophylseryltyrosylglycylleucyl-N$^\delta$, N$^\omega$-bis[adamantyl-(1)-oxycarbonyl]-arginylprolylglycinamide (XXI). The protected decapeptide XXI is converted to pyroglutamylhistidyltryptophylseryltyrosylglycylleucylarginylprolylglycinamide (XXII) as is shown in Chart I; Example I.

CHART VI; EXAMPLE VI. PART A.

Pyroglutamylhistidyltryptophylseryltyrosine (X) is coupled with glycine benzyl ester (XXXVI) via the DCI method to give the protected hexapeptide XXXVII. Pyroglutamylhistidyltryptophylseryltyrosylglycine benzyl ester (XXXVII) is subjected to hydrogenolysis with 5% palladium on charcoal for removal of the benzyl ester. The resulting hexapeptide, pyroglutamylhistidyltryptophylseryltyrosylglycine (XXXVIII) is coupled with leucyl-N$^\delta$,N$^\omega$-bis[adamantyl-(1)-oxycarbonyl]-arginylprolylglycinamide (XVIII) by the DCI method to give the protected decapeptide XXI. Pyroglutamylhistidyltryptophylseryltyrosylglycylleucyl-N$^\delta$,N$^\omega$-bis-[adamantyl-(1)-oxycarbonyl]-arginyl prolylglycinamide (XXI) is converted successively into the decapeptide, pyroglutamylhistidyltryptophylseryltyrosylglycylleucylarginylprolylglycinamide (XXII) as shown in Chart I; Example I.

Melting points were performed on a Thomas-Hoover capillary melting point apparatus and are uncorrected.

Microanalyses were performed by the Mikroanalytisches Laboratorium, Bonn, Federal Republic of Germany. On tlc (silica gel G), $R^1_f$, $R^2_f$, $R^3_f$, $R^4_f$, and $R^5_f$ refer to the systems of n-butanol:glacial acetic acid:ethyl acetate:water (1:1:1:1); chloroform:methanol:ammonia solution (60:45:20); ethanol:water (7:3); chloroform:methanol (9:1) and ethyl acetate: pyridine:glacial acetic acid; water (5:5:1:3), respectively. The nmr spectra were measured at 60 Hz on a Varian Associates A-60 spectrometer (tetramethylsilane or sodium 2,2-dimethyl-2-silapentane-5-sulfonate) and the chemical shifts are expressed in $\tau$ values. The optical rotations were measured on a Pekin-Elmer Model 141 digital readout polarimeter. All amino acids used as starting material were purchased as the pure L-isomers. Amino acid analyses of the final peptides were carried out with a Beckman Amino Acid Analyzer Model 120 on samples which were hydrolyzed with 4% thioglycolic acid in 6N hydrochloric acid for 3 hr in an evacuated sealed tube at 138° C.

N-tert-Butyloxycarbonyl-O-benzyltyrosylglycine Benzyl Ester (LVI)

N-tert-Butyloxycarbonyl-O-benzyltyrosine (LV) (27.6 g) and dry tetrahydrofuran (100 ml) at 0° C. were treated successively with triethylamine (10.3 ml), ethyl chloroformate (7.1 ml) and, after an hr, glycine benzyl ester tosylate (XXXVI) (25 g) and triethylamine (10.3 ml) in dry tetrahydrofuran (100 ml). After being stirred at room temperature during 16 hr, the reaction mixture was evaporated to dryness. The residue was dissolved in ethyl acetate (400 ml) and the solution was washed with 5% citric acid (2×50 ml), 5% sodium bicarbonate solution (2×50 ml) and water 2×50 ml). The organic layer was dried ($Na_2SO_4$) and evaporated. The residue was crystallized from methanol-n-hexane to afford the (LVI); 35.7 g, yield 93%; m.p. 101°–4° C; $[\alpha]_D^{22} + 1.2°$ (c 1.29, methanol); $R_f^4$ 0.91; single spot with chlorine/tolidine and iodine reagents. $\tau_{CDCl_3}$ 2.65, d, 10H benzylic aromatic protons; 4.86, s,2H and 4.98,s,2H benzylic methylene protons and 8.64,s,9H butyloxy protons.

Anal. Calcd. for $C_{30}H_{34}N_2O_6$; C, 69.48; H, 6.61; N, 5.40 Found: C, 68.98; H, 6.87; N, 5.45.

N-tert-Butyloxycarbonyl-O-benzylseryl-O-benzyltyrosylglycine Benzyl Ester (LIX).

A solution of the protected dipeptide ester (LVI) (10 g), in trifluoroacetic acid (15 ml), was stirred at room temperature during 15 min. The reaction mixture was evaporated in vacuo to afford the dipeptide trifluoroacetate (LVIII). This material was neutralized with triethylamine and added to the mixed anhydride solution of N-tert-butyloxycarbonyl-O-benzylserine (LVII) (5 g) which was prepared as described for the preparation of (LVI).

After being stirred at room temperature during 16 hours, the reaction mixture was evaporated and the residue was treated with cold water. The precipitate was collected and washed well with 5% citric acid, 5% sodium bicarbonate solution and water, respectively. The crude product was purified by crystallization from ethyl acetate-petroleum ether to afford the tripeptide (LIX); 9.8 g yield 83%; mp. 92°–5°C; $[\alpha]_D^{22}$ −3.2° (c 1.59, chloroform); $R_f^4$, 0.92; single spot with chlorine/-tolidine and iodine reagents. $\tau_{CCl_4}$ 2.76 and 2.82, 15H, benzylic aromatic protons, 4.95,s,2H; 5.12,s,2H and 5.60,s,2H benzylic methylene protons and 8.65,s,9H N-tert-butyloxy group.

Anal. Calcd. for $C_{40}H_{45}N_3O_8$: C, 69.05; H, 6.52; N, 6.04. Found C, 68.76; H, 6.65; N, 5.99.

O-Benzylseryl-O-benzyltyrosylglycine Benzyl Ester Trifluoracetate (LX)

The N-tert-butyloxycarbonyl-tripeptide (LIX) (9.5 g) was treated with trifluroacetic acid (20 ml) at 0° C. After being stirred at room temperature during 10 min., the reaction mixture was evaporated in vacuo to dryness. The residue was treated with anhydrous ether and the white precipitate was collected, and purified by crystallization from methanol-ether to afford (LX); 8.5 g, yield 88%; mp. 143°–5°, (dec.); $[\alpha]_D^{22} + 2.9°$ (c 0.92, methanol); $R_f^4$ 0.84; single spot with ninhydrin and chlorine/tolidine reagents.

Anal. Calcd. for $C_{35}H_{37}N_3O_6 \cdot CF_3COOH$: C, 62.62; H, 5.39; N, 5.92. Found: C, 62.52; H, 5.63; N, 5.56

Pyroglutamylhistidyltryptophanyl-O-benzylseryl-O-benzyltyrosylglycine Benzyl Ester (LXI)

The tripeptide (IV) (5.4 g) and 1-hydroxybenzotriazole (1.82 g) in dry dimethylformamide (50 ml), were treated with dicyclohexylcarbodimide (2.7 g) at 0°C. After being stirred at room temperature during 2 hr, the tripeptide (LX) (8.5 g) and triethylamine (1.7 ml) in dry dimethylformamide (50 ml) were added. After 36 hrs. the reaction mixture was filtered and the filtrate was evaporated in vacuo. The residue was washed with water and then recrystallized from ethanol to give the (LXI); 8.3 g, yield 69%; mp. 197°–200° C. (dec.); $[\alpha]_D^{22}$ −2.8° (c 1.23, glacial acetic acid); $R_f^1$, 0.78; $R_f^2$, 0.95; $R_f^3$, 0.66; single spot with Pauly, Ehrlich and iodine reagents.

Anal. Calcd. for $C_{57}H_{59}N_9O_{10}$ : C, 66.46; H, 5.77; N, 12.24. Found: C, 66.24; H, 6.00; N, 11.95.

Pyroglutamylhistidyltryptophanyl-O-benzylseryl-O-benzyltyrosylgylcine (LXII)

A solution of the hexapeptide ester (LXI) (2.6 g), in ethanol (50 ml), was treated with sodium hydroxide solution (8N, 5ml). After 20 min. at room temperature, the reaction mixture was acidified with glacial acetic acid, and evaporated in vacuo to dryness. The resulting precipitate was rinsed with water, and purified by crystallization from ethanol to afford the (LXII); 2 g yield 84%; mp. 171°–5°C. (dec.); $[\alpha]_D^{22}$ −0.9° (c 0.68, glacial acetic acid); $R_f^1$, 0.71; $R_f^2$, 0.59; single spot with Pauly, Ehrlich and iodine reagents.

Anal. Calcd. for $C_{50}H_{53}N_9O_{10}$ : C, 63.88; H, 5.68; N, 13.41. Found: C, 63.60; H, 5.99; N, 13.19.

N-Benzyloxycarbonylleucyl-N$^\delta$,N$^\omega$-bis[adamantyl-(1)-oxycarbonyl]-arginine(LXIV)

N-Hydroxysuccinimido-N-benzyloxycarbonylleucinate (700 mg) was added to a solution of N$^\delta$, N$^\omega$-bis[adamantyl-(1)-oxycarbonyl]-oxycarbonyl]-arginine (1 g) and triethylamine (0.3 ml) in dry dimethylformamide (20 ml). After 16 hrs, the reaction mixture was evaporated in vacuo, and the residue was crystallized from methanol-water to afford the (LXIV); 1.6 g, yield 87%; mp. 125°–130° C; $[\alpha]_D^{22}$ −7.2° (c 2.63, methanol); $R_f^4$ 0.58; single spot with iodine reagent.

Anal. Calcd. for $C_{42}H_{59}N_5O_9$. C, 64.84; H, 7.64; N, 9.00. Found: C, 64.37; H, 7.66; N, 8.75.

N-Benzyloxycarbonylleucyl-N δ, N ω -bis[adamantyl-(1)-oxycarbonyl]-arginyl-prolyl-glycinamide (XVI)

A solution of the dipeptide (LXIV) (1.55 g) and 1-hydroxybenzotriazole (0.3 g) in dry dimethylformamide (20 ml) were treated with dicyclohexylcarbodiimide (0.45 g) at 0° C. After being stirred during 2 hr. prolylglycinamide (0.35 g) was added. The reaction mixture was stirred during 48 hr. The mixture was filtered, evaporated, and the resulting peptide was washed with 5% citric acid, 5% sodium bicarbonate solution, and water, respectively. This material was purified by preparative chromatography on silica gel to obtain (XVI); 0.84 g, yield 45%; mp. 125°–130°C. (dec.); $[\alpha]_D^{22}$ −31.0 (c 1.48, methanol); $R_f^4$, 0.76; single spot with chlorine/tolidine and iodine reagents; $\tau_{MeOH-d_4}$ 2.60,s,5H. aromatic protons; 4.92,s,2H, benzylic methylene protons; 7.82,s and 8.30,s, adamantyl group.

Anal. Calcd. for $C_{49}H_{70}N_8O_{10}·1.5H_2O$: C, 61.42; H, 7.68; N, 11.70. Found: C, 61.44; H, 7.39; N, 11.35.

Pyroglutamylhistidyltryptophanyl-O-benzylseryl-O-benzyltyrosylglycylleucyl-N δ, N ω -bis[adamantyl-(1)-oxycarbonyl]-arginylprolylglycinamide (LXIII)

The protected tetrapeptide (XVI) (680 mg), in absolute ethanol (30 ml) containing 5% palladium on charcoal as catalyst, was hydrogenated at 1 atm. After being stirred at room temperature during an hour, the reaction mixture was filtered and evaporated in vacuo to afford (XVIII). This product, in dry dimethylformamide (10 ml), was added into a solution of dimethylformamide (20 ml) containing the protected peptide (LXII) (680 mg), 1-hydroxybenzotriazole (140 mg) and dicyclohexylcarbodiimide (150 mg). After being stirred at room temperature during 16 hr, the reaction mixture was filtered, and the filtrate was evaporated in vacuo. The resulting precipitate was collected by addition of water (1.2 g). A portion of this (850 mg) was purified by column chromatography on silica gel with elution by chloroform-methanol (8:2 v/v) to afford LXIII, (380 mg yield 43%) which was crystallized from ethanol; mp. 165°–170°C (dec.); $[\alpha]_D^{22}$ −10.6 (c 0.98, glacial HOAc); $R_f^1$, 0.81; $R_f^2$, 0.96; $R_f^3$, 0.63; single spot with Pauly, Ehrlich and iodine reagents.

Anal. Calcd. for $C_{91}H_{115}N_{17}O_{17}$: C, 63.58; N, 6.74; N, 13.85. Found: C, 63.17; H, 6.65; N, 13.90.

Pyroglutamylhistidyltryptophanylseryltyrosylglycyl-leucylarginylprolylglycinamide LRH) (XXII).

The protected decapeptide (LXIII) (340 mg), in methanol (20 ml) and glacial acetic acid (2 ml) containing 5% palladium on barium sulfate as catalyst, was hydrogenated at 1 atm. After being stirred at room temperature during 25 hr, the reaction mixture was filtered and evaporated in vacuo to dryness. The residue was then treated with trifluoroacetic acid (5 ml) at 0° C. After 15 min, at room temperature, the reaction mixture was evaporated in vacuo. The resulting decapeptide was washed well with anhydrous ether, and was dissolved in 1% acetic acid (100 ml). This solution was passed through a AG1-X8 (OH⁻) (1×15 cm) column and the filtrate was evaporated in vacuo to dryness. The residue was dissolved in water (10 ml). The solution was applied to a CMC column (1×20 cm) which was eluted with each of the following pH 6.6 ammonium acetate buffers: 0.005, 0.01, 0.025, 0.05, 0.075 and 0.1 M. Individual fractions (3 ml each) were collected at a flow rate of approximately 3 ml/min. The desired peptide (22) was located in the 0.075 M. eluates by the Pauly reaction. These eluates were pooled and the solvent was evaporated. The residue was lyophilized to constant weight with water affording a white powder; 98 mg, yield 42%; $[\alpha]_D^{22}$ −33.6° (c 1.16, methanol); $R_f^1$, 0.64; $R_f^3$, 0.37; $R_f^5$, 0.49; single spot with Pauly, Ehrlich, Sakaguchi and chlorine/tolidene reagents. Amino acid rations in acid hydrolysate: Glu 1.00, His 1.10, Trp 0.59, Ser 0.78, Tyr 0.86, Gly 2.00, Leu 0.86, Arg 1.04, Pro 0.98, NH₃ 1.14.

Anal. Calcd. for $C_{55}H_{75}N_{17}O_{13}·2CH_3COOH$. C, 54.40, H, 6.42, N, 18.28; Found: C, 54.37; H, 6.41.

| RELEASE OF LUTEINIZING HORMONE IN A RAT ASSAY BY THE SYNTHETIC LRH | | |
|---|---|---|
| Dose Level Syn. LRH | LH Levels M μg/ml serum | |
| | before | after |
| 5 ng | <4 | 57 |
| | <4 | 138 |
| 10 ng | <4 | 88 |
| | <4 | 148 |
| 25 ng | 5 | 242 |
| | 5.4 | 226 |
| 50 ng | 5.4 | 204 |
| | 4 | 97 |

CHART VI; EXAMPLE VI. PART B.

Melting points were performed in a Thomas-Hoover capillary melting point apparatus and are uncorrected. Microanalyses were performed by the Chemalytics, Inc., Tempe, Arizona, and where given are within ±0.4% of the theoretical values. Thin layer chromatography was performed on silica gel G (E. Merck). Rf¹, Rf², and Rf³ refer to the systems n-BuOH-glacial HOAc—EtOAc—H₂O (1:1:1:1), CHCl₃—MeOH—NH₄OH (60:45:20) and EtOH—H₂O (7:3), respectively. Optical rotations were measured on a Perkin-Elmer Model 141 Digial Readout Polarimeter. All amino acid analyses of the final peptides were carried out with a Beckman Amino Acid Analyzer Model 119 on samples which were hydrolyzed in 6N HCl containing 4% thioglycollic acid and in an evacuated sealed tube at 110° overnight.

Z-Ser-Tyr-Gly-OEt (LVIII)

Z-Ser-Tyr-NH-NH₂¹(LV) (102 g), in H₂O (1.11) containing concentrated HCl (80 ml) and glacial HOAc (110 ml), was treated with NaNO₂ (15 gm) in H₂O (150 ml) at 0° C. After being stirred for 30 minutes, the reaction mixture was shaken with ethyl acetate (2 liters) and the organic layer was washed well with cold water and 5% NaHCO₃ soln. This solution was added to Gly-OEt·HCl (LVII) (42 gm) in H₂O (100 ml) and Et₃N (102 ml). The reaction mixture was stirred at 0° C for 16 hours, and the separated organic layer was washed well with 5% NaHCO₃, 5% citric acid and finally with brine. The dried (Na₂SO₄) solution was evaporated, in vacuo to dryness and the residue was purified by crystallization from EtOH to afford 28.2 gm (23.5%); of the tripeptide, Z—Ser—Tyr—Gly—OEt (LVIII): m.p. 168°–170°C; $[\alpha]_D^{22}$ −24.0 (c, 1.37, MeOH); Rf¹ 0.91 and Rf³ 0.70, single spot with I₂ reagent.

Anal. Calcd. for $C_{24}H_{29}N_3O_8$ C, 59.12; H, 5.99; N, 8.62. Found: N, 8.41.

Ser—Tyr—Gly—OEt (LIX)

A mixture of Z-Ser-Tyr-Gly-OEt (LVIII) (52.5 gm) in absolute EtOH (1.51), and 10% palladium on charcoal (10 gm) was hydrogenolyzed at room temperature under one atmosphere of hydrogen with vigorous stirring for 24 hours. The palladium on charcoal was filtered and washed thoroughly with EtOH. The filtrate was evaporated under reduced pressure and the residue was crystallized (EtOH) to afford 26.4 gm (70%) of Ser—Tyr—Gly—OEt (LIX): m.p. 176°–177° C; $[\alpha]_D^{22}$ + 2.6° (c, 1.84, MeOH), $Rf^1$ 0.72 and $Rf^3$ 0.50 single spot with $I_2$ reagent. Amino Acid analysis gave Ser 0.8; Tyr 1.0; Gly 1.0.

pGlu—His—Trp—Ser—Tyr—Gly—OEt (LX)

Ser-Tyr-Gly-OEt (LIX) (15.1 gm) and 1-hydroxybenzotriazole (5 gm), in dry DMF (150 ml) were treated with DCI (7 gm) at 0°C. The mixture was stirred at room temperature for 3 hours, and then pGlu—His—Trp—OH (IV) (11.8 gm) in dry DMF (100 ml) was added. After 48 hours, the reaction mixture was filtered and the filtrate was evaporated in vacuo. Treatment of the residue with EtOAc and acetone left the crude hexapeptide ester (LX) as a yellow precipitate. Chromatography over silica gel with $CHCl_3$—MeOH, afforded 14.5 gm. (55%) of the pure hexapeptide ester: $[\alpha]_D^{22}$–18.4 (c, 1.05, MeOH) $Rf^1$ 0.69, $Rf^2$ 0.86, and $Rf^3$ 0.43, single spot with Pauly and $I_2$ reagents.

Anal. Calcd. for $C_{38}H_{45}N_9O_{10}$: C, 57.93; H, 5.76; N, 16.00. Found: N, 15.80.

pGlu—His—Trp—Ser—Tyr—Gly—OH (XXXVIII)

The above hexapeptide ester (LX) (11 gm) in MeOH (200 ml) was treated at room temperature with NaOH (3.45 gm) in $H_2O$ (10 ml). After 30 minutes, the reaction mixture was neutralized at 0°C with 1 equivalent of 6N HCl (14.8 mg), and evaporated to dryness, in vacuo, at 30°C. The residue was rinsed with cold water (3 × 50 ml) and purified by crystallization (EtOH) to afford 8.2 gm (77%) of the pure hexapeptide acid (XXXVIII): m.p. 180°–184°C (dec); $[\alpha]_D^{22}$–13.1 (c, 1.35; $H_2O$); $Rf^1$ 0.53, and $Rf^3$ 0.66 single spot with Pauly and $I_2$ reagent. Amino acid analysis gave Glu 1.15; His 0.78; Trp 0.91; Ser 0.96; Tyr 1.01; Gly 1.0.

Anal. Calcd. for $C_{36}H_{41}N_9O_{10}$·MeOH: C, 56.12; H, 5.73; N, 15.92. Found: C, 56.47; H, 5.96; N, 16.03.

Boc—$N^G$—Tos—Arg—Pro—Gly—$NH_2$ (LXII)

Boc—$N^G$—Tos—Arg—OH (LXI) (21 gm) and 1-hydroxybenzotriazole (7 gm) in dry DMF (200 ml) were treated with DCI (11 gm) at 0°C and stirred for 3 hours. Pro—Gly—$NH_2$ (XII) (9 gm) in dry DMF (100 ml) was added and stirring was continued for a further 48 hours. The filtered mixture was evaporated and the residue was partitioned between $H_2O$ (500 ml) and $CHCl_3$ (600 ml). The dried ($Na_2SO_4$) organic layer was evaporated and left 38 g of product. Column chromatograhy over silica gel with $CH_2Cl_2$—MeOH afforded 18 gm (63%) of the pure tetrapeptide (LXIV): $[\alpha]_D^{22}$–20.7 (c, 2.72, MeOH); $Rf^1$ 0.82 and $Rf^3$ 0.66 single spot with $I_2$ reagent. Amino acid analysis gave Arg 0.9; Pro 1.0; Gly 1.0; and $NH_3$ 0.9.

Anal. Calcd. for $C_{28}H_{39}N_7O_7S$: C, 51.61; H, 6.76; N, 16.86. Found: C, 50.60; 6.85; N, 16.89.

TFA·$N^G$—Tos—Arg—Pro—Gly—$NH_2$ (LXIV)

The above tripeptide (LXII) (18 gm) was treated with TFA (150 ml) for 30 minutes at room temperature. The reaction mixture was evaporated and the residue was treated with anhydrous $Et_2O$ and filtered to afford 17.8 gm (97%), of the pure TFA salt (LXIV): $[\alpha]_D^{22}$–1.3 (c, 1.27, MeOH); $Rf^1$ 0.62, $Rf^2$ 0.87 and $Rf^3$ 0.37. Single spot with ninhydrin and $I_2$ reagent.

Anal. Calcd. for $C_{20}H_{31}N_7O_5S$·$CF_3COOH$: C, 44.36; H, 5.42; N, 16.46. Found: C, 44.22; H, 5.38.

Z—Leu—$N^G$—Tos—Arg—Pro—Gly—$NH_2$ (LXV)

Z-Leu-OSu (LXIII) (10.8 gm), and the above TFA salt (LXIV) (17.8 gm) in DMF (200 mg) and $Et_3N$ (8.4 ml), were stirred at room temperature for 24 hours. The reaction mixture was evaporated in vacuo and the resulting peptide was partitioned between $H_2O$ and $CHCl_3$. The dried ($Na_2SO_4$) organic layer was evaporated and crystallized from acetone-MeOH to afford 17.7 gm (80%) of pure LXV: m.p. 138°–140°C; $[\alpha]_D^{22}$ –35.4 (c, 1.16, MeOH); $Rf^1$ 0.86 and $Rf^3$ 0.68, single spot with $I_2$ reagent. Amino acid analysis gave Leu 1.1; Arg 0.9; Pro 1.0; Gly 1.0; $NH_3$ 0.9.

Anal. Calcd. for $C_{34}H_{48}N_8O_8S$: C, 56.03; H, 6.64; N, 15.37. Found: C, 55.75; H, 6.73; N, 15.01.

Leu—Arg—Pro—Gly—$NH_2$·2HF (LXVI)

Z—Leu—$N^G$—Tos—Arg—Pro—Gly—$NH_2$ (LXV) (15.9 gm) was treated with dry ($CoF_3$) HF (60 ml) for 20 minutes at 0°C. The reaction mixture was evaporated in vacuo and the residue was treated with $H_2O$ (300 ml) and filtered. The filtrate was lyophilized to leave 10.5 gm, (97%) of the dihydrofluoride salt (LXVI): $Rf^2$ 0.23; single spot with ninhydrin and $I_2$ reagent. Amino acid analysis gave Leu 1.10; Arg 0.98; Pro 1.15; Gly 1.00; $NH_3$ 0.98.

pGlu—His—Trp—Ser—Tyr—Gly—Leu—Arg—Pro—Gly—$NH_2$ (XXII) (LHRH)

A stirred mixture of pGlu—His—Trp—Ser—Tyr—Gly—OH (XXXVIII) (16.6 gm) and 1-hydroxybenzotriazole (3 gm) in dry DMF (250 ml) was treated with DCI (4.5 gm) at 0°C and after 3 hours, the dihydrofluoride salt of Leu—Arg—Pro—Gly—$NH_2$ (LXVI) (10.5 gm) and $Et_3N$ (3.1 ml) in dry DMF were added and stirring was continued at room temperature for a further 36 hous. The reaction mixture was evaporated in vacuo and the residue was treated with $H_2O$ (200 ml). The insoluble DCI-urea was removed and the filtrate was evaporated in vacuo to afford 38 g of crude LHRH. A portion of this (6.47 gm) in 1% AcOH (250 ml) was passed over Bio-Rad AG1-8 (OAc) (1×15 cm) and the filtrate was evaporated in vacuo. The residue, in $H_2O$ (15 ml), was chromatographed over CMC (4.5 × 27 cm) and eluted in a stepwise manner with $NH_4OAc$ buffers of pH 6.9: (0.005, 0.01, 0.025, 0.075 and 0.1 M). The pooled LHRH fractions, located in the 0.075 M eluate by the Pauly reaction, were lyophilized. The LHRH (3 gm) was further purified by gel filtration over Bio-Gel P-2 (400 gm) (110 cm × 2.5 cm) with 1.3% AcOH. Individual fractions (5 ml) were collected at a flow rate of about 5 ml.min and the pure LHRH was located in fractions 21–31 by the Pauly reaction and by tlc. Fractions showing one spot on tlc were pooled and lyophilized to constant weight affording 2.85 gm. (59%) of pure pGlu—His—Trp—Ser—Tyr—Gly—Leu—Arg—Pro—Gly—$NH_2$ (XXII) (LHRH):

$[\alpha]_D^{22}$ —33.9 (c, 0.66, MeOH); $[\alpha]_D^{22}$ —46.6 (c, 0.73, 1% AcOH); $Rf^1$ 0.64 and $Rf^3$ 0.37, single spot with Pauly, chlorine-tolidine and $I_2$ reagents. Amino acid analysis gave Glu 1.08; His 0.99; Trp 0.87; Ser 0.85; Tyr 0.98; Gly 2.07; Leu 1.04; Arg 1.02; Pro 0.97; $NH_3$ 1.08.

Anal. Calcd. for $C_{55}H_{75}N_{37}O_{13}\cdot 2CH_3COOH$, 2 $H_2O$: C, 52.94; H, 6.54; N, 17.79. Found: C, 53.19; H, 6.73; N, 17.84.

REFERENCES FOR CHART VI; EXAMPLE VI PART B.

1. H. Hofmann, T. A. Thompson, H. Yajima, E. T. Schwartz and H. Inouye, J. Am. Chem. Soc., 82, 3715 (1960).
2. C. Y. Bowers, Ann. N.Y. Acad. Sci., 185, 263 (1971).

| IN VITRO ASSAY$^2$ OF SYNTHETIC DECAPEPTIDE (LRH) ng LH/ml medium | | | | | |
|---|---|---|---|---|---|
| $P_1$ | $P_2$ | $I_3$ | $I_4$ | $I_5$ | $I_6$ |
| Dose | | 0.1 ng | 0.1 ng | 0.3 ng | 0.3 ng |
| 18 | 18 | 525 | 560 | >714 | >714 |
| Dose | | 3 ng | 3 ng | 9 ng | 9 ng |
| 33 | 90 | >714 | >714 | >714 | >714 |

CHART VII; EXAMPLE VII.

Pyroglutamylhistidyltryptophylseryltryosylglycine (XXXVIII) is coupled with L-leucine benzyl ester (XXXIX) via the DCI method to give the heptapeptide benzyl ester XL. Pyroglutamylhistidyltryptophylseryltyrosylglycylleucine benzyl ester (XL) is subjected to hydrogenolysis with 5% palladium on charcoal for removal of the benzene group. The resulting heptapeptide, pyroglutamylhistidyltryptophylseryltyrosylglycylleucine (XLI) is coupled with N $\delta$ ,N $\omega$ -bis[adamantyl-(1)-oxycarbonyl]-arginylprolylglycinamide (XV) by the method to give the protected decapeptide XXI. Pyroglutamylhistidyltryptophylseryltyrosylglycylleucyl-N $\delta$ ,N $\omega$ -bis[adamantyl-(1)-oxycarbonyl]-arginylprolylglycinamide (XXI) is converted successively into the decapeptide, pyroglutamylhistidyltryptophylseryltyrosylglycylleucylarginylprolylglycinamide (XXII) as shown in Chart I; Example I.

CHART VIII; EXAMPLE VIII.

Pyroglutamylhistidyltryptophylseryltyrosylglycylleucine (XLI) is converted to the activated ester (XIII) with hydroxysuccinimide, which is then coupled with N $\delta$ ,N $\omega$ -bis[adamantyl-(1)-oxycarbonyl]-arginine (XLIII) to give the protected octapeptide XLIV. Pyroglutamylhistidyltryptophylseryltyrosylglycylleucyl N $\delta$ ,N $\omega$ -bis[adamantyl-(1)-oxycarbonyl]-arginine (XLIV) is coupled with prolylglycinamide (XII) via the DCI method to give the protected decapeptide (XXI). Pyroglutamylhistidyltryptophylseryltyrosylglycylleucyl-N $\delta$ ,N $\omega$ -bis[adamantyl-(1)-oxycarbonyl]-arginylprolylglycinamide (XXI) is converted successively into the decapeptide, pyroglutamylhistidyltryptophylseryltyrosylglycylleucylarginylprolylglycinamide (XXII) as shown in Chart I; Example I.

CHART IX; EXAMPLE IX.

Pyroglutamylhistidyltryptophylseryltyrosylglycylleucyl-N $\delta$ ,N $\omega$ -bis[adamantyl-(1)-oxycarbonyl]-arginine (XLIV) is coupled with L-proline benzyl ester (XLV) by the DCI method to give the blocked nonapeptide XLVI. Pyroglutamylhistidyltryptophylseryltyrosylglycylleucyl-N $\delta$ ,N $\omega$ -bis[adamantyl-(1)-oxycarbonyl]-arginylproline benzyl ester (XLVI) is subjected to hydrogeolysis, with 5% palladium on charcoal for removal of the benzyl ester, to give pyroglutamylhistidyltryptophylseryltyrosylglycylleucyl-N $\delta$ ,N $\omega$ -bis[adamantyl-(1)-oxycarbonyl]-arginylproline (XLVII), which is coupled with glycinamide (XLVIII) to give the protected decapeptide (XXI). Pyroglutamylhistidyltryptophylseryltyrosylglycylleucyl-N $\delta$ ,N $\omega$ -bis[adamantyl-(1)-oxycarbonyl]-arginyl-prolylglycinamide (XXI) is successively converted into the decapeptide, pyroglutamylhistidyltryptophylseryltyrosylglycylleucylarginylprolylglycinamide (XXII) as shown in Chart I; Example I.

CHART X; EXAMPLE X.

Using a solid-phase peptide synthesis method and coupling the appropriate protected amino acids one by one using DCI as coupling reagent the protected heptapeptide resin, t-butyloxycarbonyl-O-benzyl-seryl-O-benzyl-tyrosylglycylleucyl-nitro-arginylprolylglycin resin, (IL), is obtained. This heptapeptide (IL) is then removed from the resin by ammonolysis giving tert-butyloxycarbonyl O-benzyl-seryl-O-benzyl-tyrosylglycylleucyl-nitro-arginylprolylglycinamide (L). The tert-butyloxycarbonyl group is then removed using trifluoroacetic acid (TFA) to give O-benzyl-seryl-O-benzyl-tyrosylglycylleucyl-nitro-arginylprolyl-glycinamide·TFA (LI), which is coupled with pyroglutamylhistidyltryptophan (IV) mediated by DCI giving the protected decapeptide pyroglutamylhistidyltryptophanyl-O-benzyl-seryl-O-benzyl-tyrosylglycylleucyl-nitro-arginylprolylglycinamide (LII). The decapeptide (LII) is then subjected to hydrogenolysis using 5% palladium on barium sulfate for removal of the benzyl groups and the nitro group to give pyroglutamylhistidyltryptophanylseryltyrosylglycylleucylarginylprolylglycinamide (XXII). $R_f$=0.64 of heptapeptide (L) in butanol-acetic acid-ethylacetate-water in a ratio of 1:1:1:1 on silica gel G.

Melting points were performed on a Thomas Hoover melting point apparatus and are uncorrected. Microanalyses were performed by the Mikroanalytisches Laboratorium Bonn, West Germany. $R_f^1$, $R_f^2$, $R_f^3$, values refers to the systems: n-BuOH:glacial HOAc:EtOAc:$H_2O$, (1:1:1:1); $CHCl_3$:MeOH:conc. $NH_4OH$, (60:45:20); and EtOH:$H_2$), (7:3), respectively. The nmr spectra were recorded on a Varian Associates A60 spectrometer ($Me_4Si$ as internal standard). The optical rotations were measured on a Perkin-Elmer Model 141 digital readout polarimeter using a microcell. All of the amino acids which were used were purchased as pure L-isomers. A solid-phase peptide synthesis was carried out with a Beckman Model 990 Peptide Synthesizer, and the amino acid analyses were done with a Beckman Model 121 Amino Acid Analyzer which was connected to a Beckman Model 126 Data Analyzer. All of the countercurrent distribution. Amino acid analyses of sample V frm distribution: Gly 1.00; His 1.00; Trp 0.92; Ser 0.98; Tyr 0.78; Gly 2.06; Leu 0.88; Arg 1.07; Pro 1.16; NH₃ 1.00.

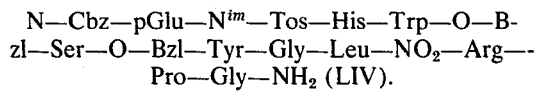

t-Boc-Gly resin (2.0 g, 1.4 mM Gly) was used and the same reaction cycle as described for compound II was utilized. The first seven amino acids were introduced as described for II; then, t-Boc-Trp, t-Boc-His(Tos) and Z-gGlu were added. The t-Boc-amino acids (3.5 mM of each) were dissolved in CH₂Cl₂ (11 ml) except for t-Boc-Arg(NO₂) and t-Boc-Trp when DMF (11 ml) was used as the solvent. DCI (3.5 mM) was added in CH₂Cl₂ (3 ml). After the introduction of t-Boc-Trp, 1% 1,4-butanedithiol was added in step (b). The Z-pGlu—His(Tos)—Trp—Ser(Bzl)—Tyr(Bzl)—Gly—Leu—Arg—(NO₂)—Pro—Gly-resin LIII was dried in vacuo over night, and was then suspended in MeOH-dioxane-NH₃, as described for II, and the mixture was stirred for 40 hr at room temperature. Evaporation and drying in vacuo over night yielded crude LIV which was purified by recrystallization from MeOH giving 790 mg; (yield 33 %, based on Gly attached to the resin). Single spot in tlc to Ehrlich and chlorine-tolidine reagents. Amino acid analyses after HCl hydrolyses: Glu 0.98; His(Tos) 0.99; Ser 0.79; Tyr 0.45; Gly 2.0; Leu 0.92; Arg(NO₂) 0.98 (corr. for Orn); Pro 1.0.

pGlu—His—Trp—Ser—Tyr—Gly—Leu—Arg—Pro—Gly—NH₂ (LRH) (XXII)

Compound LIV (220 mg), anisole (1.5 ml), and a 10-fold molar excess of Met were mixed and dry HF (15 ml) was then distilled into the reaction vessel kept at −60°. The temperature was then adjusted to 0°, and the reaction mixture was stirred for 45 min. The HF and the anisole were removed in vacuo, and the residue was dissolved in 1% HOAc and lyophilized. The material was purified by CCD. The product showed identical R_f values in thin layer chromatography as for the decapeptide from Scheme 1; sngle product positive to Pauly, Ehrlich, Sakaguchi and chlorine-tolidine reagents. Amino acid analyses on sample VI from countercurrent distribution: Glu 0.84, His 0.92, Ser 0.74, Tyr 0.84, Gly 2.00, Leu 0.86, Arg 1.03, Pro 1.28.

COUNTERCURRENT DISTRIBUTION

The product of the synthesis of Scheme 1 (sample I) was subjected to counter-current distribution involving 100 transfers. The two-phase system used was n-butanol:pyridine:0.1% acetic acid 5:3:11. A protein analysis of every second tube according to the Folin-Lowry method[1] indicated the presence of several products in all the tubes; the contents of tubes 60–88 (maximum at K ~ 1.8) showed a peak. After removal of the solvent from these combined fractions, the material was redistributed in the same solvent system. The apparatus was set on a recycling operation to permit a 200-transfer distribution.

The center fractions of the peak representing tubes 147–159 were combined and assayed as sample III. Further purification of sample III by 100 transfers in H₂O:n-BuOH:HOAc(5:4:1) was achieved. The center fractions representing tubes 29–36 were combined and assayed as sample IV. This material was taken for a final distribution in 100 transfers in the same solvent. Tubes 18–25 (peak at K ~ 0.24) yielded sample V.

In order to establish proof of purity of the decapeptide, the theoretical distribution was calculated and compared to the peak obtained for the last distribution. Calculations were made on the assumption that the fraction at the center of the peak had the highest purity, and the K-value would be the most accurate.

The substance in the tube with the distribution maximum was equated to the observed optical density of 0.446, and the concentrations in the other tubes were expressed as O.D. values which were calculated[6] from the expression:

$$T_{n,r} = \frac{n!}{r!(n-r)!} \left(\frac{1}{\epsilon+1}\right)^n \epsilon^r$$

with $r$ = number of tube
$n$ = number of transfers
$\epsilon$ = extraction factor = $K \cdot \dfrac{V_{upper\ phase}}{V_{lower\ phase}}$
$T_{n,r}$ = fraction in the $r^{th}$ tube in a distribution of n transfers.

In this way, the theoretical and the experimental curves have been adjusted to equal heights which permits comparison of the shape of both curves.

Table 2 shows the theoretical and experimental values of the optical densities for K = 0.24.

TABLE 2

| Tube No. | CCD DATA ON SYNTHETIC LRH | |
|---|---|---|
| | O.D. exp. | O.D. calc. |
| 14 | 0.083 | 0.008 |
| 16 | 0.128 | 0.023 |
| 18 | 0.147 | 0.069 |
| 20 | 0.199 | 0.156 |
| 22 | 0.264 | 0.277 |
| 24 | 0.374 | 0.391 |
| 26 | 0.446 | 0.446 |
| 28 | 0.397 | 0.414 |
| 30 | 0.337 | 0.316 |
| 32 | 0.269 | 0.200 |
| 34 | 0.193 | 0.105 |
| 36 | 0.134 | 0.047 |
| 38 | 0.111 | 0.017 |

The curves are in good agreement at both sides of the maximum. The experimental concentrations on the outer parts of the slopes are higher than the calculated ones, probably because of diminishing accuracy of the protein determination with the very small quantity of substance.

The product of synthesis by Scheme 2 was purified in three steps. After the first 100-transfer distribution in n-BuOH:pyridine:0.1% acetic acid, 200 transfers were made in the same solvent system using the material in tubes 64–92.

Five fractions (tubes 130–141; 142–154; 155–161; 162–175 and 176–186) were chemically assayed by tlc. The plates indicated the presence of a second product contained in increasing quantities in tubes 142–186. Tubes 130–154 were combined, and the material was distributed in 100 transfers in n-BuOH:HOAc:H₂O, and the contents of tubes 18–25 were combined and assayed as sample VI.

RELEASE OF LUTEINIZING HORMONE

The in vivo bioassays for release of LH were performed in Sprague-Dawley female rats after ovariectomy. The rats were injected with 50 μg of estradiol benzoate and 25 mg of progesterone 72 hours before samples for amino acid analysis were hydrolyzed with 4% thioglycolic and, 6N HCl for 3 hr, in an evacuated sealed tube at 138° C.

All distributions were carried out with a 100-tube automatic countercurrent fractionator of E-C Apparatus Corporation. Each tube contained 10 ml of solvent in the lower phase and 13–15 ml in the upper phase. A distribution in more than 100 tubes could be attained by setting the apparatus on a recycling operation. At the end of each distribution, aliquots from the tubes were taken for the protein analysis according to Folin and Lowry.[1] The fractions were then lyophilized to remove the solvents. All solvents were of Reagent Grade and were redistilled before use.

t-Boc-O-Bzl-Ser-O-Bzl-Tyr-Gly-Leu-NO$_2$-Arg-Pro-Gly-NH$_2$(L).

The protected heptapeptide amide, L was prepared by the solid-phase peptide synthesis procedure of Merrifield[2]. t-Boc-Gly was attached to a Bio-Beads SX-1 chloromethylated resin (200–400 mesh) with a capacity of 1.75 meq. of Cl/g resin by refluxing in ethanol in the presence of Et$_3$N, as described[2]. An aliquot of the t-Boc-resin was deprotected with HCl in dioxane and then hydrolyzed. Gly was determined in the amino acid analyzer to be 0.7 mM per g resin. t-Boc-Gly-resin (3.0 g; 2.1 mM of Gly) was added to the reaction vessel and the following steps were used to couple each new amino acid; (a) washing with dioxane (3×24 ml); (b) prewash with 4N HCl in dioxane (24 ml); (c) removal of the t-Boc group using 4N HCl in dioxane (24 ml) for 30 min; (d) washing with dioxane (3×24 ml); (e) washing with CH$_2$Cl$_2$(3×24 ml); (f) prewash with 10% Et$_3$N in CH$_2$Cl$_2$ (24 ml); (g) neutralization of the HCl salt with 10% Et$_3$N in CH$_2$Cl$_2$ (24 ml) for 10 min. (h) washing with CH$_2$CL$_2$ (3×24 ml); (i) addition of 5.25 mM of the appropriate protected t-Boc amino acid in CH$_2$Cl$_2$ (17 ml) and mixing for 10 min; (j) addition of DCI (5.25 mM) in CH$_2$Cl$_2$ (4 ml) followed by a reaction period of 4 hrs; (k) washing with CH$_2$Cl$_2$ (3×24 ml). Each prewashing period was for 1.5 min. The following t-Boc proteced amino acids were successively added, Pro, Arg(NO$_2$), Leu, Gly, Tyr(Bzl), Ser (Bzl). When t-Boc-Arg (NO$_2$) was introduced, step (h) was followed by a wash with DMF (3×24 ml), and the t-Boc-Arg(NO$_2$) was dissolved in DMF. Step (i) was then followed by another DMF wash (3×24 ml.).

The success of the coupling reactions were monitored by the semiquantitative ninhydrin reaction as described by Kaiser et al.[9] The t-Boc-Ser(Bzl)—Tyr(Bzl)—Gly—Leu—Arg(NO$_2$)—Pro—Gly—resin (IL) was dried in vacuo overnight; 4.8 g of material was obtained, which was suspended in MeOH-dioxane (4:1 v/v) (50 ml) saturated with NH$_3$ at −2°. The mixture was stirred in a tightly stoppered flask at room temperature for 36 hrs. After filtration and evaporation of the solvent in vacuo, the residue was purified by column chromatography on silica gel G. Starting with chloroform as elution solvent and by increasing the polarity of the solvent by using methanol, the protected heptapeptide amide, L, was eluted with CHCl$_3$:MeOH (9:1 v/v). After precipitation from methanol: ether, L was obtained. 797 mg (35% yield based on attached Gly to the resin) $[\alpha]_D^{22} = -43.3$ (c 1.0, methanol) $R_f^1$ 0.80; $R_f^2$ 0.97; $R_f^3$ 0.73; single spot to chlorine-tolidine reagent. NMR (MeOH-d$_4$) τ=2.62 and 2.70 (ArH; 5H each); 4.98 (ArCH$_2$; 2H) 6.25 (ArCH$_2$; 2H); 8.70 (C(CH$_3$)$_3$; 9H); 9.10 (CH(CH$_3$)$_2$; 6H). Amino acid analyses Gly 0.90; Tyr 0.28; Gly 2.00; Leu 0.93; Arg-(NO$_2$) 0.62 (uncorrected); Pro 1.06. Tyr is known to give a low value in the presence of Arg (NO$_2$)[3].

O—Bzl—Ser—O—Bzl—Tyr—Gly—Leu—NO$_2$—Arg—Pro—Gly—NH$_2$·TFA salt (LI).

Compound L (322 mg) was dissolved in trifluoroacetic acid (TFA) (3 ml) for 5 min. The solvent was then evaporated and the product was dried over KOH in vacuo for 12 hrs; tlc showed a single product positive to the ninhydrin and -chlorine-tolidine reagents with $R_f^1$ 0.73, $R_f^3$ 0.68.

pGlu—His—Trp Bzl Ester (III)

Pyrolutamylhistidine[4] (723 mg), 1-OH-benzotriazole[5] (250 mg), tryptophan benzyl ester HCl (900 mg), and Et$_3$N (0.35 ml) in dry DMF (25 ml) were treated with DCI (560 mg) at 0° C. After being stirred at room temperature during 48 hr., the reaction mixture was evaporated in vacuo to dryness. The residue was partitioned with CHCl$_3$ and H$_2$O, and an oily product was separated between these two solvents. The oily product was collected and purified by recrystallization from MeOH/EtOAc to afford the tripeptide 1.16 g (yield 79%), m.p. 235°–238° C (dec) $[\alpha]_D^{22}$—6.8° (c 1.54, glacial HOAc), $R_f^1$ 0.72, $R_f^2$ 0.89, and $R_f^3$ 0.59, single spot with Pauly, Ehrlich, Cl-tolidine and I$_2$ reagents. Anal. C$_{29}$H$_{30}$N$_6$O$_5$·H$_2$O; C, H, N.

pGlu— His—Trp (IV)

Pyroglutamylhistidyltryptophan benzyl ester (780 mg) in MeOH (30 ml) and glacial HOAc (10 ml) with 5% Pd/C as catalyst was hydrogenated during 2 hours at room temperature at 1 atm. The reaction mixture was filtered and evaporated to give the tripeptide; 422 mg. (yield 64%); m.p. 188°–190° C (dec); $R_f^1$ 0.58; $R_f^2$ 0.64; $R_f^3$ 0.50; single spot with Pauly, Ehrlich, and Cl-tolidine reagents.

pGlu—His—Trp—O—Bzl—Ser—O—Bzl—Tyr—Gly—Leu—NO$_2$—Arg—Pro—Gly—NH$_2$ (LII)

Pyroglutamylhistidyltryptophan (147 mg) was mixed with 1-OH-benzo-triazole[5] (45 mg) and DCI (62 mg) in dry DMF (5 ml) and the mixture ws stirred at 0° for 1 hour; the stirring was then continued at room temperature for 1 hour. Compound III (326 mg) and Et$_3$N (0.045 ml) were then added at 0° and the reaction mixture was left at room temperature for 5 hours. After evaporation of the solvent in vacuo (40°C), the residue was purified by preparative thin layer chromatography on silica gel G using methanol-chloroform (3:7 v/v) as the developing solvent. This procedure gave 180 mg, (yield 45%) of LII; $R_f^1$ 0.65; $R_f^2$ 0.84; $R_f^3$ 0.63; single spot positive to Pauly, Ehrlich and chlorine-tolidine reagents. Amino acid analyses; Glu 1.0; His 1.1; Ser 0.80; Tyr 0.61; Gly 2.0; Leu 0.98; Arg(NO$_2$) (corr)1.0; Pro 1.1. Arg(NO$_2$) is corrected for Orn formed in the hydrolysis.

pGlu—His—Trp—Ser—Tyr—Gly—Leu—Arg—Pro—Gly—NH$_2$(LRH) (XXII).

Compound LII (30 mg) was dissolved in MeOH-glacial acetic acid (9:1 v/v) (10 ml) and was hydrogenated over Pd on BaSO$_4$ (60 mg) at room temperature and atmospheric pressure for 40 hrs. Evaporation of the solvent in vacuo yielded I; 15 mg (yield 60%) $R_f^1$ 0.64; $R_f^3$ 0.37; positive to Pauly, Ehrlich, Sakaguchi and chlorine-tolidine reagents. The product was purified by injection of the test samples according to the method of Ramirez and McCann[7]. Under anesthesia, blood was collected from the jugular vein, and the test samples were injected into the same vein. Serum assays for LH were performed in duplicate by the double antibody radioimmuno assay of Niswender et al.[8] The LH results are expressed in terms of mµg/ml of LER-1240-2-0.60 NIH-LH-SI units/mg. The data for samples I–VI are in Table 1.

Chart II. Example II.

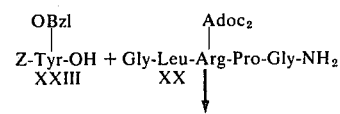

TABLE I

RELEASE OF LUTEINIZING HORMONE IN A RAT ASSAY BY THE SYNTHETIC LUTEINIZING RELEASING HORMONE

| Sample | Dose ng. | LH Levels ng/ml serum Before | After | Sample | Dose ng. | LH Levels ng/ml serum Before | After |
|---|---|---|---|---|---|---|---|
| I | 25 | <4 | 134 | IV | 1 | 4.2 | 68 |
|  |  | <4 | 127 |  |  | <4 | 34 |
|  | 50 | <4 | >285 |  | 5 | 4 | 120 |
|  |  | <4 | >285 |  |  | 5.4 | 218 |
|  |  |  |  |  | 25 | <41 | 166 |
| II | 1 | 5 | 12 |  |  | 5.6 | 262 |
|  |  | 4 | 13 |  |  |  |  |
|  | 5 | <4 | 42 | V | 0.5 | 5 | 17 |
|  |  | <4 | 38 |  |  | <4 | 10 |
|  | 10 | 4 | 262 |  | 1 | <4 | 16 |
|  |  |  |  |  |  | 4 | 23 |
| III | 5 | <4 | 146 |  | 5 | 4 | 83 |
|  |  | 4 | 65 |  |  | <4 | 114 |
|  |  | <4 | 85 |  |  |  |  |
|  | 10 | 3.2 | 113 | VI | 1 | 5.5 | 9 |
|  |  | 5.4 | 176 |  |  | 5 | 6 |
|  |  |  |  |  | 5 | 4 | 18 |
|  |  |  |  |  |  | 4 | 28 |
|  |  |  |  |  | 25 | 6 | 220 |
|  |  |  |  |  |  | 4 | >284 |

REFERENCES FOR EXAMPLE X.

1. O. H. Lowry, N. J. Rosebrough, A. L. Farr, and R. J. Randall, J. Biol. Chem., 193, 265 (1951).
2. R. B. Merrifield, J. Amer. Chem. Soc., 85, 2149 (1963).
3. M. Moritz and R. Wade, Anal. Biochem., 41, 446 (1971).
4. J. K. Chang, H. Sievertsson, B. L. Currie, K. Folkers, and C. Y. Bowers, J. Med. Chem., 14, 484 (1971).
5. W. Konig and R. Geiger, Chem. Ber., 103, 788 (1970).
6. B. Williamson and L. C. Craig, J. Biol. Chem., 168 687 (1947).
7. V. D. Ramirez and S. M. McCann, Endocrinology, 73, 193 (1963).
8. G. D. Niswender, A. R. Midgley, Jr., S. E. Monroe, and L. E. Reichert, Jr., Proc. Soc. Exp. Biol. Med., 128, 807 (1968).
9. E. Kaiser, R. L. Colescott, C. D. Bossinger, and P. T. Cook, Anal. Biochem., 34, 595 (1970).

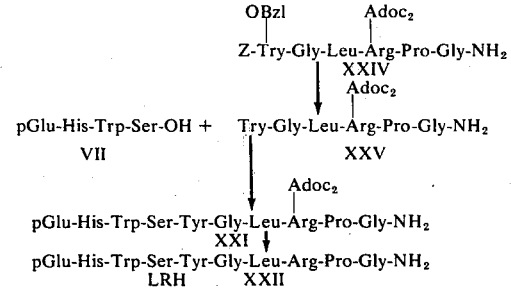

Chart I. Example I.

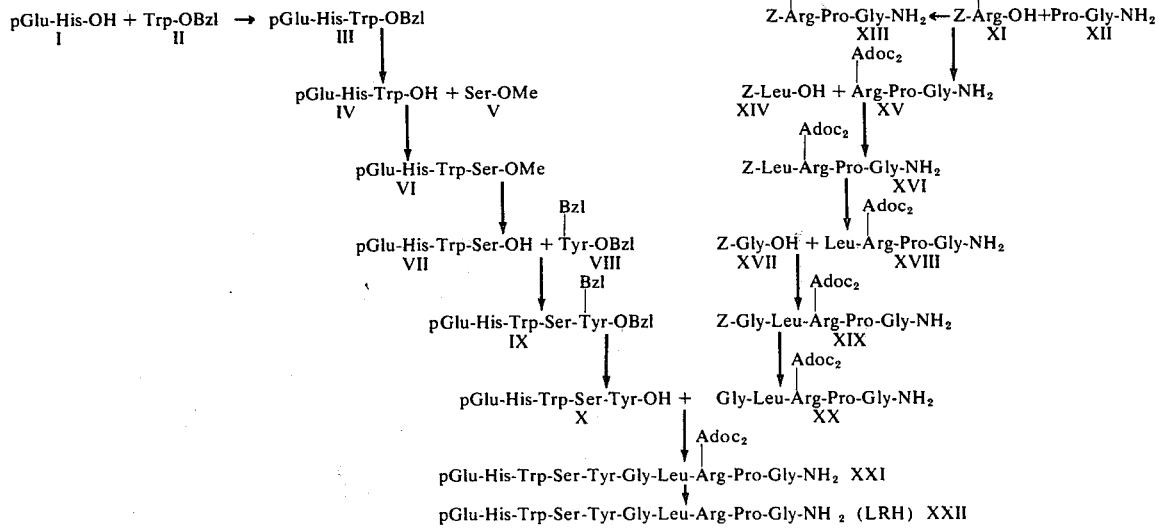

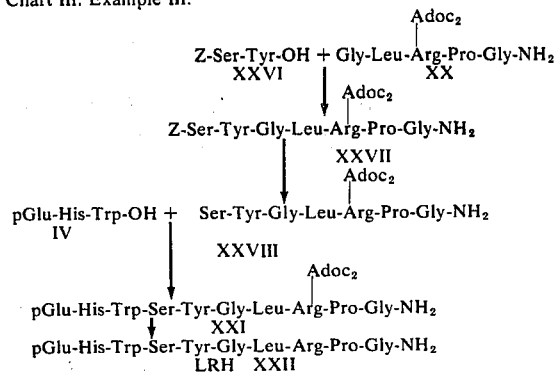
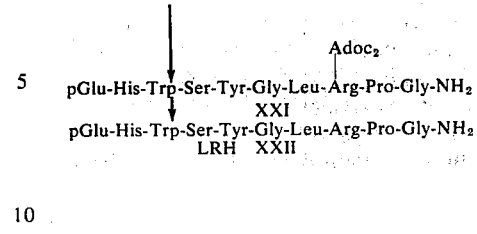
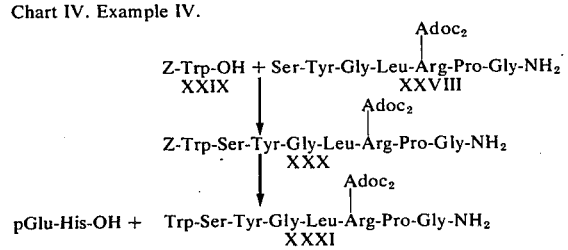
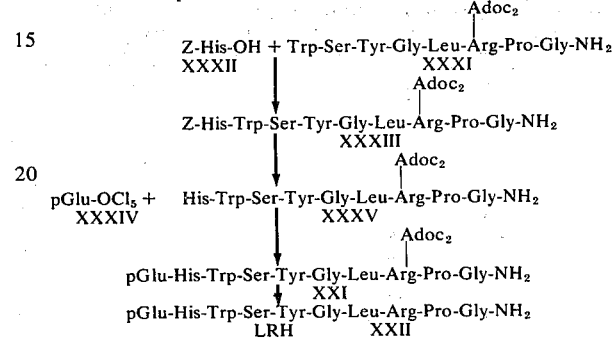
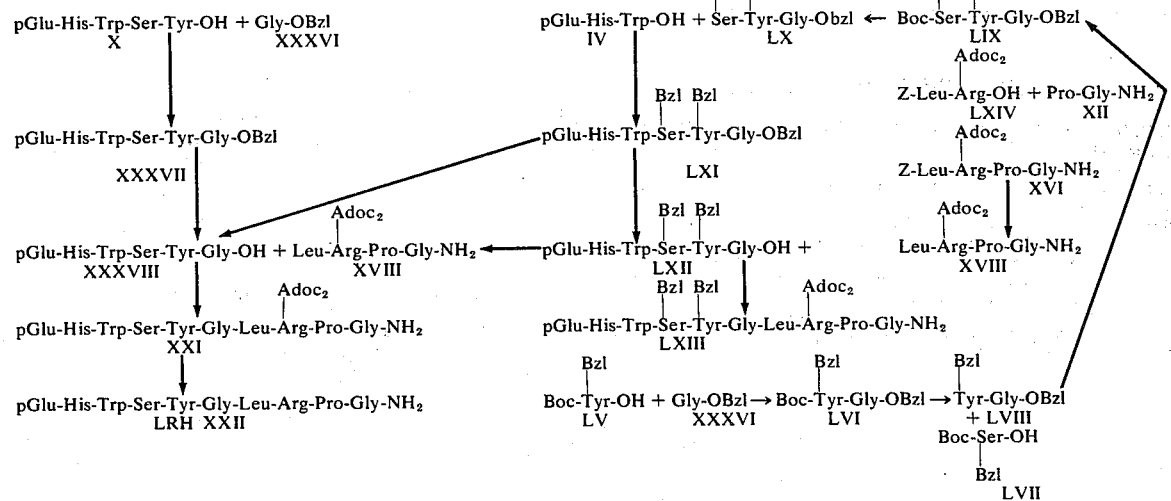
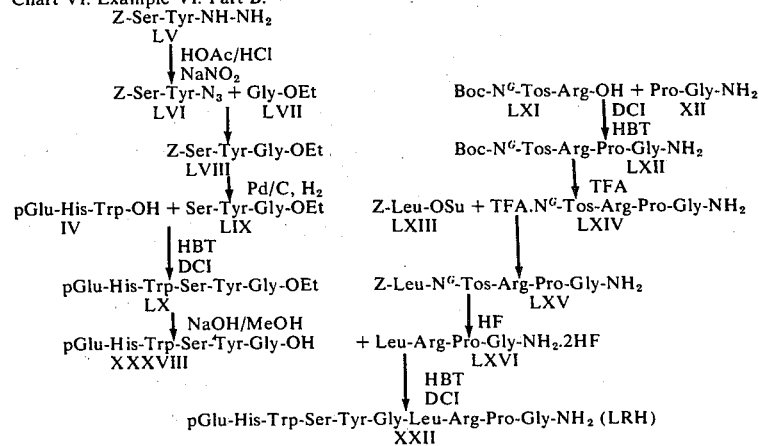

Chart VII. Example VII.

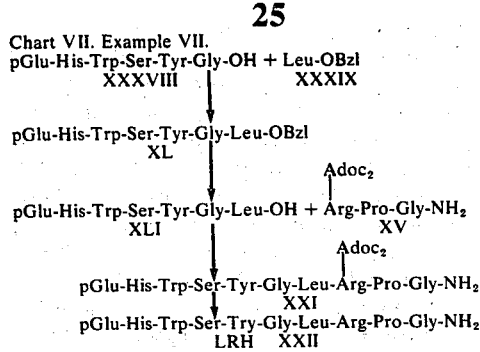

Chart VIII. Example VIII.

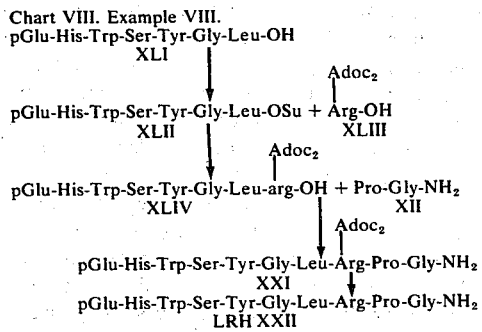

Chart IX. Example IX.

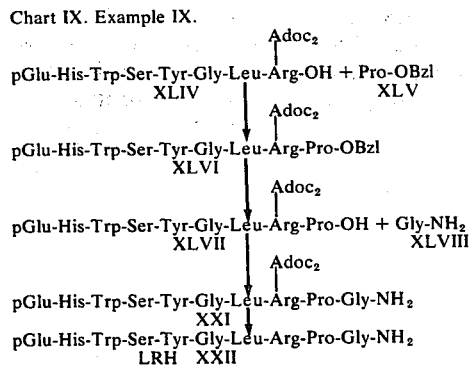

Chart X. Example X.

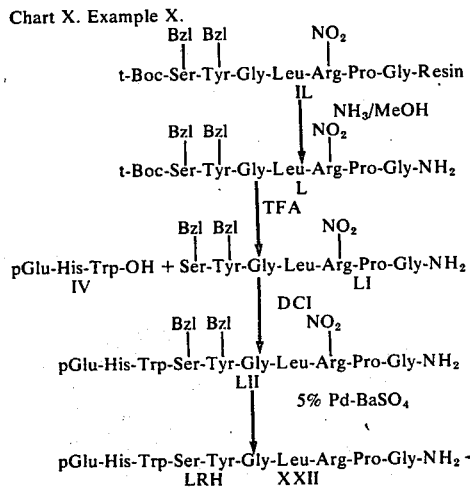

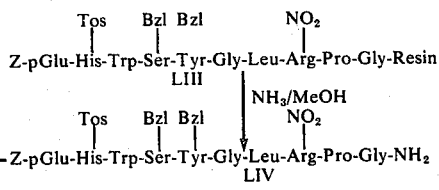

What is claimed:

1. A method for prepared the decapeptide, L-pyroglutamyl-L-histidyl-L-tryptophanyl-L-seryl-L-tyrosyl-glycyl-L-leucyl-L-arginyl-L-prolyl-glycinamide, by coupling by the DCI method the hexapeptide, L-pyroglutamyl-L-histidyl-L-tryptophanyl-L-seryl-L-tyrosyl-glycine; produced by saponification of the hexapeptide ethyl ester, said hexapeptide ethyl ester produced by coupling the tripeptide, L-pyroglutamyl-L-histidyl-L-tryptophan, produced by coupling L-pyroglutamyl-L-histidine with L-tryptophan benzyl ester by the DCI method and then hydrogenolysis of the benzyl ester, with the tripeptide ethyl ester, L-seryl-L-tyrosyl-glycine ethyl ester by the DCI method, said tripeptide ethyl ester produced by conversion of N-carbobenzyloxy-L-seryl-L-tyrosine hydrazide to the corresponding azide which is added to glycine ethyl ester to give N-carbobenzyloxy-L-seryl-L-tyrosyl-glycine ethyl ester and then hydrogenolysis; with the tetrapeptide, L-leucyl-L-arginyl-L-prolyl-glycinamide, produced by treatment of the blocked tetrapeptide, N-carbobenzyloxy-L-leucyl-$N^G$-para-toluenesulfonyl-L-arginyl-L-prolyl-glycinamide, with hydrogen fluoride; said blocked tetrapeptide produced by coupling N-hydroxysuccinimido-$N^\alpha$-carbobenzyloxy-L-leucinate with the tripeptide, $N^G$-para-toluenesulfonyl-L-arginyl-L-prolyl-glycinamide, said tripeptide produced by cleavage of the tert-butyloxycarbonyl group from the blocked tripeptide, $N^\alpha$-tert-butyloxycarbonyl-$N^G$-para-toluenesulfonyl-L-arginyl-L-prolylglycinamide, said blocked tripeptide produced by coupling $N^\alpha$-tert-butyloxycarbonyl-$N^G$-para-toluenesulfonyl-L-arginine with L-prolyl-glycinamide by the DCI method.

2. A method for producing the decapeptide, L-pglutamyl-L-histidyl-L-tyrptophanyl-L-seryl-L-tyrosyl-glycyl-L-leucyl-L-arginyl-L-prolyl-glycinamide, from the protected forms of the amino acids consisting of glutamic acid or pyroglutamic acid, histidine, tryptophan, serine, tryosine, glycine, leucine, arginine, proline, and glycine; said method comprising diimide or active ester coupling of the appropriately, protected sequences: the nonapeptide obtained from coupling the adjacently-named amino acids pyroglutamic acid, histidine, tryptophan, serine, tyrosine, glycine, leucine, arginine, proline with the remining amino acid glycine; or, the octapeptide obtained from coupling the adjacently-named amino acids pyroglutamic acid, histidine, tryptophan, serine, tyrosine, glycine, leucine, arginine with the dipeptide obtained from coupling the remaining adjacently-named amino acids proline, glycine; or, the heptapeptide obtained from coupling the adjacently-named amino acids pyroglutamic acid, histidine, tryptophan, serine, tyrosine, glycine, leucine with the tripeptide obtained from coupling the remaining adjacently-named amino acids arginine, proline, glycine; or, the hexapeptide obtained from coupling the adjacently-named amino acids pyroglutamic acid, histidine, tryptophan, serine, tyrosine,, glycine with the tetrapeptide obtained from coupling the remaining adjacently-named amino acids leucine, arginine, proline, glycine; or, the pentapeptide obtained from coupling the adjacently-named amino acids pyroglutamic acid, histidine, tryptophan, serine, tyrosine with the pentapeptide obtained from coupling the remaining adjacently-named amino acids glycine, leucine, arginine, proline, glycine; or, the tetrapeptide obtained from coupling the adjacently-named amino acids pyroglutamic acid, histidine, trypophan, serine with the hexapeptide obtained from coupling the remaining adjacently-named amino acids tyrosine, glycine, leucine, arginine, proline, glycine; or, the tripeptide obtained from coupling the adjacently-named amino acids pyroglutamic acid, histidine, tryptophan with the heptapeptide obtained from coupling the remaining adjacently-named amino acids serine, tyrosine, leucine, arginine, proline, glycine; or, the dipeptide obtained from coupling the adjacently-named amino acids pyroglutamic acid, histidine with the octapeptide obtained from coupling the remaining adjacently-named amino acids tryptophan, serine, tyrosine, glycine, leucine, arginine, proline, glycine; or, pyroglutamic acid with the nonapeptide obtained from coupling the remaining adjacently-named amino acids histidine, tryptophan, serine, tyrosine, glycine, leucine, arginine, proline, glycine; followed by deprotection of the protecting groups to give said decapeptide, α said amino acids being provided in protected form, from the α-amino and side chain amino protective groups consisting of carbobenzyloxy-, tosyl-, phthalyl-, benzyl-, trityl-, formyl-, t-butoxyloxycarbonyl-, nitro-, and adamantlyloxycarbonyl; the side chain hyroxy and protective groups consisting of benzyl-, para-substituted benzyl-, acyl-, and alkyl-; and, the carboxyl protective groups consisting of methyl ester, ethyl ester, benzyl ester, t-butyl ester, and dinitrophenyl ester.

3. The method of claim 2 wherein said method includes protonation for the protection of the guanidine moiety of said arginine or said arginine and said histidine being provided in protective form by the protective groups tosyl, benzyl, and dinitrophenyl.

4. The method of claim 2 wherein said method is conducted pursuant to solid phase synthesis of the protected heptapeptide resin part of said decapeptide, said protected heptapeptide resin part being obtained from successively coupling the adjacently-named protected amino acids glycine, proline, arginine, leucine, glycine, tyrosine and serine, with the cleavage of said protected heptapeptide from the resin; and coupling said protected heptapeptide to the tripeptide, p-glutamyl-histidyl-trytophan, said tripeptide being obtained from coupling the adjacently-named protected amino acids p-glutamic acid, histidine, tryptophan to give the decapeptide after deprotection or, by solid phase sequential coupling of said adjacently-named protected amino acids: glycine, proline, arginine, leucine, glycine, tyrosine, serine, tryptophan, histidine and p-glutamic acid, to give the protected decapeptide resin, followed by cleavage from the resin and deprotection of said protected decapeptide to give the decapeptide.

* * * * *